United States Patent
Wentzel et al.

(10) Patent No.: US 6,468,271 B1
(45) Date of Patent: Oct. 22, 2002

(54) DEVICE AND METHOD FOR PERCUTANEOUS MYOCARDIAL REVASCULARIZATION

(75) Inventors: David E. Wentzel, Issaquah; Ryan Kaveckis, Seattle, both of WA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/256,958

(22) Filed: Feb. 24, 1999

(51) Int. Cl.$^7$ .............................................. A61B 18/18
(52) U.S. Cl. ............................................ 606/34; 606/41
(58) Field of Search ........................... 606/34, 35, 41, 606/42, 45–50; 607/98, 107, 113, 115, 116, 119, 122

(56) References Cited

U.S. PATENT DOCUMENTS

| | | | |
|---|---|---|---|
| 4,196,734 A | * 4/1980 | Harris | 606/31 |
| 5,125,926 A | * 6/1992 | Rudko et al. | 606/19 |
| 5,735,280 A | 4/1998 | Sherman et al. | 128/600.03 |
| 5,766,164 A | 6/1998 | Mueller et al. | 606/15 |
| 5,769,843 A | 6/1998 | Abela et al. | 606/10 |
| 5,782,823 A | 7/1998 | Mueller | 606/7 |
| 5,785,702 A | 7/1998 | Murphy-Chutorian et al. | 606/7 |
| 5,800,450 A | 9/1998 | Lary et al. | 606/180 |
| 5,807,384 A | 9/1998 | Mueller | 606/7 |
| 5,807,388 A | 9/1998 | Jeevanandam et al. | 606/15 |
| 5,810,836 A | 9/1998 | Hussein et al. | 606/108 |
| 5,827,203 A | 10/1998 | Nita | 601/2 |
| 5,832,929 A | 11/1998 | Rudko et al. | 128/898 |
| 5,840,059 A | 11/1998 | March et al. | 604/53 |
| 5,840,075 A | 11/1998 | Mueller et al. | 606/7 |
| 5,855,577 A | 1/1999 | Murphy-Chutorian et al. | 606/7 |
| 5,860,951 A | 1/1999 | Eggers et al. | 604/49 |
| 5,871,495 A | 2/1999 | Mueller | 606/185 |
| 5,873,366 A | 2/1999 | Chim et al. | 128/898 |
| 5,873,855 A | 2/1999 | Eggers et al. | 604/114 |
| 5,878,751 A | 3/1999 | Hussein et al. | 128/898 |
| 5,885,272 A | 3/1999 | Aita et al. | 606/7 |
| 5,885,276 A | 3/1999 | Ammar et al. | 606/21 |
| 5,891,133 A | 4/1999 | Murphy-Chutorian | 606/7 |
| 5,893,848 A | 4/1999 | Negus et al. | 606/41 |
| 5,951,543 A | * 9/1999 | Brauer | 606/10 |
| 5,971,980 A | * 10/1999 | Sherman | 606/34 |

FOREIGN PATENT DOCUMENTS

| | | |
|---|---|---|
| DE | 195 37 084 A1 | 4/1997 |
| EP | 0 553 576 A1 | 8/1993 |
| EP | 0 858 779 A1 | 8/1998 |
| WO | WO 98/19614 | 5/1998 |
| WO | WO 98/25533 | 6/1998 |
| WO | WO 98/27877 | 7/1998 |
| WO | WO 98/30144 | 7/1998 |
| WO | WO 98/31281 | 7/1998 |
| WO | WO 98/33557 | 8/1998 |
| WO | WO 98/38916 | 9/1998 |
| WO | WO 98/38925 | 9/1998 |
| WO | WO 98/39038 | 9/1998 |
| WO | WO 98/49963 | 11/1998 |
| WO | WO 98/49964 | 11/1998 |
| WO | WO 99/04708 | 2/1999 |
| WO | WO 99/04709 | 2/1999 |
| WO | WO 99/07296 | 2/1999 |
| WO | WO 99/08612 | 2/1999 |

* cited by examiner

Primary Examiner—Linda C. M. Dvorak
Assistant Examiner—R. Kearney
(74) Attorney, Agent, or Firm—Crompton, Seager & Tufte LLC

(57) ABSTRACT

Methods and devices for performing percutaneous myocardial revascularization without disrupting the blood pumping activity of the heart. A percutaneous myocardial revascularization system including an active electrode disposed at the end of a catheter and a radio frequency generator coupled to the active electrode for delivering radio frequency energy thereto. Radio frequency energy is selectively applied to the active electrode when the active electrode is properly positioned and when the heart is not in a vulnerable stage of the cardiac rhythm.

8 Claims, 8 Drawing Sheets

DEVICE AND METHOD FOR PERCUTANEOUS MYOCARDIAL REVASCULARIZATION

RELATED APPLICATION

The present application is related to U.S. patent application Ser. No. 09/256,831, filed by the same assignee on even date herewith and entitled "PMR Catheter"

FIELD OF THE INVENTION

The present invention relates generally to devices and methods for promoting blood circulation to the heart muscle. More particularly, the present invention relates to devices and methods for forming holes, craters or channels in the interior walls of a heart chamber as part of a percutaneous myocardial revascularization (PMR) procedure.

BACKGROUND OF THE INVENTION

Assuring that the heart muscle is adequately supplied with oxygen is critical to sustaining the life of a patient. To receive an adequate supply of oxygen, the heart muscle must be well perfused with blood. In a healthy heart, blood perfusion is accomplished with a system of blood vessels and capillaries. However, it is common for the blood vessels to become occluded (blocked) or stenotic (narrowed). A stenosis may be formed by an atheroma which is typically a hard, calcified substance which forms on the walls of a blood vessel.

Historically, individual stenotic lesions have been treated with a number of medical procedures including coronary bypass surgery, angioplasty, and atherectomy. Coronary bypass surgery typically involves utilizing vascular tissue from another part of the patient's body to construct a shunt around the obstructed vessel. Angioplasty techniques such as percutaneous transluminal angioplasty (PTA) and percutaneous transluminal coronary angioplasty (PTCA) are relatively non-invasive methods of treating a stenotic lesion. These angioplasty techniques typically involve the use of a guidewire and a balloon catheter. In these procedures, a balloon catheter is advanced over a guidewire such that the balloon is positioned proximate a restriction in a diseased vessel. The balloon is then inflated and the restriction in the vessel is opened. A third technique which may be used to treat a stenotic lesion is atherectomy. During an atherectomy procedure, the stenotic lesion is mechanically cut or abraded away from the blood vessel wall.

Coronary by-pass, angioplasty, and atherectomy procedures have all been found effective in treating individual stenotic lesions in relatively large blood vessels. However, the heart muscle is perfused with blood through a network of small vessels and capillaries. In some cases, a large number of stenotic lesions may occur in a large number of locations throughout this network of small blood vessels and capillaries. The torturous path and small diameter of these blood vessels limit access to the stenotic lesions. The sheer number and small size of these stenotic lesions make techniques such as cardiovascular by-pass surgery, angioplasty, and atherectomy impractical When techniques which treat individual lesion are not practical a technique known as percutaneous myocardial revascularization (PMR) may be used to improve the oxygenation of the myocardial tissue. A PMR procedure generally involves the creation of holes, craters or channels directly into the myocardium of the heart. PMR was inspired in part by observations that reptilian heart muscles are supplied with oxygen primarily by blood perfusing directly from within heart chambers to the heart muscle. This contrasts with the human heart, which is supplied by coronary vessels receiving blood from the aorta. Positive clinical results have been demonstrated in human patients receiving PMR treatments. These results are believed to be caused in part by blood flowing within a heart chamber through channels in myocardial tissue formed by PMR. Increased blood flow to the myocardium is also believed to be caused in part by the healing response to wound formation. Specifically, the formation of new blood vessels is believed to occur in response to the newly created wound. This response is sometimes referred to as angiogenisis.

In addition to promoting increased blood flow, PMR may also improve the condition of a patient through denervation. Denervation is the elimination of nerve endings. Wounds created during PMR result in the elimination of nerve endings which were previously sending pain signals to the brain as a result of hibernating tissue. In one embodiment in accordance with the present invention, a fluid under pressure is forced into the wound formed by PMR. This fluid may include saline, contrast media, a therapeutic agent, a caustic agent, or any combination of these. Means for detecting contact 706 may be used to verify that electrode 30 is in contact with myocardial tissue when the fluid is delivered. Injecting a fluid including a radiopaque contrast media creates a radiopaque marker of the treatment site. Injecting a fluid including a therapeutic agent into the wound may enhance the angiogenic response of the body. Forcing fluid under pressure into the wound may also create collateral damage within an area proximate the wound. This collateral damage may include the rupturing of blood vessels, capillaries, and sinuses within the myocardium. This collateral damage will increase the healing response by angiogenisis.

A number of methods have been used to create channels in the myocardium during percutaneous myocardial revascularization. Methods of cutting include the use of knife-like cutting tools and cutting with light from a LASER. Radio frequency energy may also be used to burn or ablate channels or craters into myocardial tissue.

SUMMARY OF THE INVENTION

The present invention relates to methods and devices for performing percutaneous myocardial revascularization without interfering with the blood pumping activity of the heart. A desirable feature of the present invention is that the delivery of radio frequency energy to an area proximate the heart is discontinued when the heart is in a vulnerable period of the cardiac rhythm. A second desirable feature of the present invention is that the discharge of electrical energy stored in the heart is disallowed during vulnerable periods of each heart beat.

A system for performing percutaneous myocardial revascularization in accordance with the present invention typically includes an active electrode disposed at the end of a catheter, and a radio frequency generator coupled to the active electrode. The PMR system further includes a means for patient monitoring capable of detecting electrical activity in the heart of a patient. Radio frequency energy is selectively applied to the active electrode only when the heart is not in a vulnerable stage of the cardiac rhythm.

Embodiments of a percutaneous myocardial revascularization system in accordance with the present invention may also include provisions to assure that the active electrode is properly positioned. In one embodiment of the present invention an impedance means is coupled between the active electrode and the radio frequency generator. The impedance value of the impedance means is selected so that maximum power transfer will occur when the active electrode is in contact with the myocardial tissue of the patient's heart. To accomplish this, the impedance value of the impedance means is selected so that the impedance of the PMR system is substantially equal to the load impedance which will be encountered by the system when the active electrode contacts the myocardial tissue of the patient's heart.

An additional embodiment of the present invention includes a means for detecting contact between the active electrode and the myocardial tissue of a patient's heart. This embodiment is for use with a method of PMR during which a high level of radio frequency energy is not applied to the active electrode until contact between the active electrode and myocardial tissue has been detected. A relatively low level of radio frequency energy is utilized to detect contact between the active electrode and myocardial tissue. A high level of radio frequency energy is selectively applied to the active electrode only after contact has been verified.

A method in accordance with the present invention avoids discharging high levels of radio frequency energy into the blood. The discharge of high levels of radio frequency energy into the blood may cause complications such as platelet damage, gas bubbles, and blood clots.

DETAILED DESCRIPTION OF THE INVENTION

The following detailed description should be read with reference to the drawings, in which like elements in different drawings are numbered identically. The drawings which are not necessarily to scale, depict selected embodiments and are not intended to limit the scope of the invention.

Examples of constructions, materials, dimensions, and manufacturing processes are provided for selected elements. All other elements employ that which is known to those of skill in the field of the invention. Those skilled in the art will recognize that many of the examples provided have suitable alternatives which may be utilized.

Figure 1:
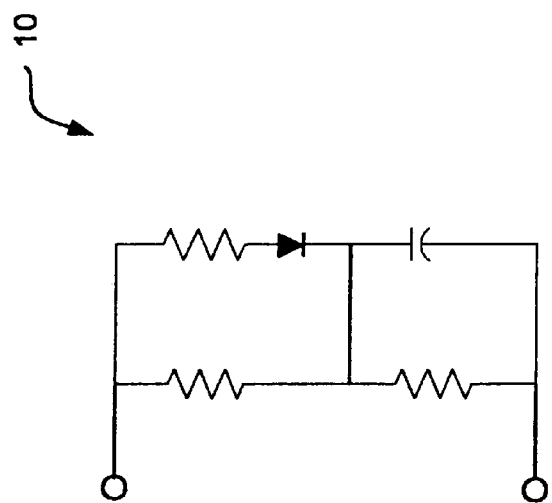
FIG. 1 is a schematic diagram of a circuit modeling the human heart muscle.

FIG. 1 is a schematic diagram of a circuit 10 modeling the human heart muscle. As shown in the circuit of FIG. 1, the endocardium and the myocardium of the heart exhibit a combination of capacitance, resistance and rectifying elements. Applicant has found that the capacitor is a dominant component in this model. The capacitive element in this model represents the ability of the heart to store an electrical charge. It is a desirable feature of the present invention that the discharge of this electrical energy is disallowed during vulnerable periods in each heartbeat.

Figure 2:
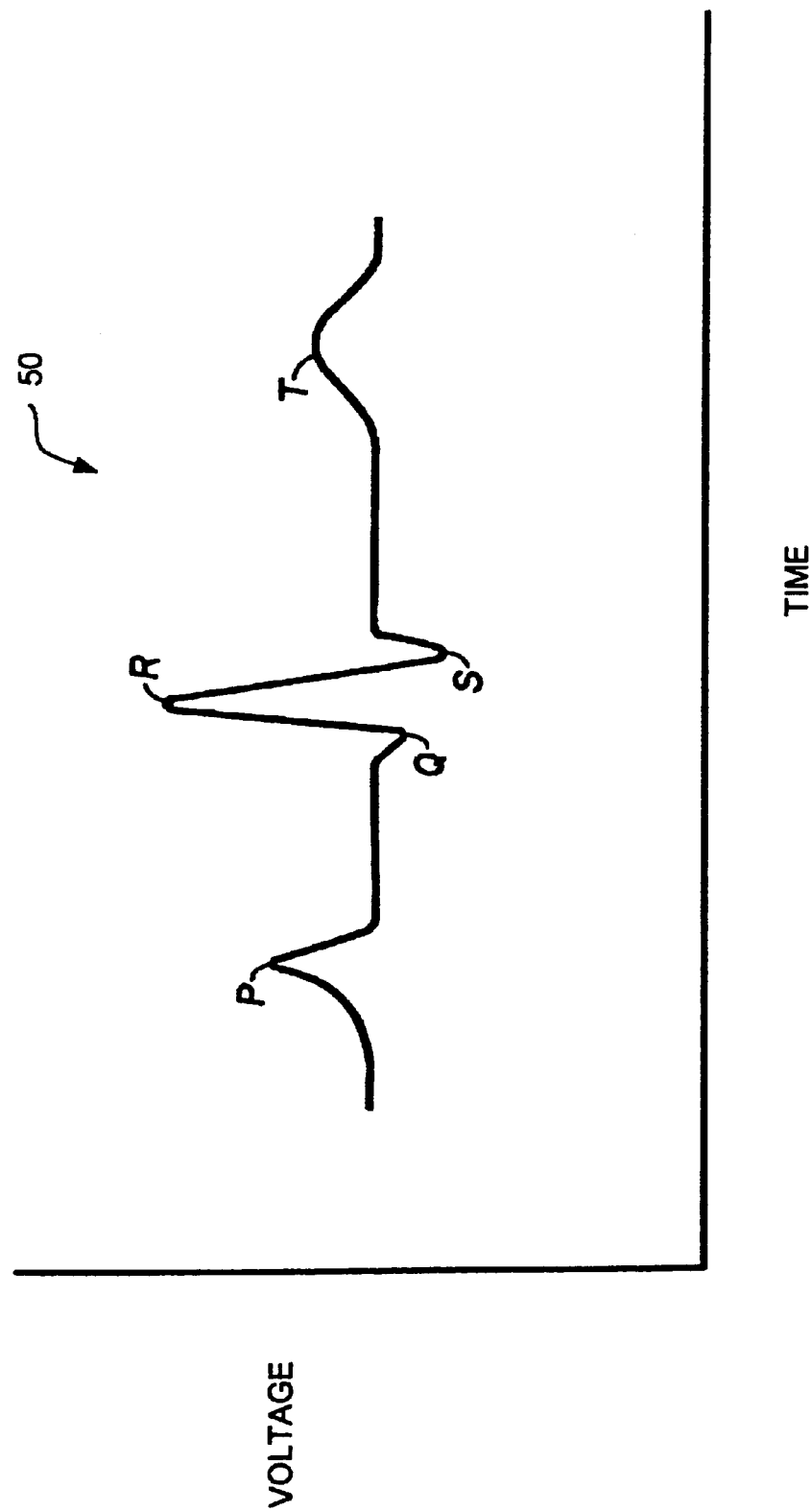
FIG. 2 is an electrocardiograph wave form representing a single heart beat.

FIG. 2 is an electrocardiograph waveform 50 representing a single heartbeat. As shown in FIG. 2, each heartbeat may be represented as a complex wave comprised of five component waves designated "P", "Q", "R", "S" and "T" waves. The first component wave is the P-wave which electronically represents an atrial beat associated with atrial depolarization which commands heart rate as a function of signals from the rest of the body depicting the required cardiac output.

The main feature of the electrocardiogram signal is the R-wave which is a generally triangular pulse representing the electrical actuation of the ventricles. The R-wave is the electrical activity in the heart which stimulates a ventricular contraction. The T-wave portion of each heartbeat follows the R wave by about 0.3 seconds. The T-wave indicates the repolarization of the ventricles. During the repolarization of the ventricles the heart rhythm is vulnerable to disruption by electrical current passing through the heart or proximate the heart. More particularly, ventricular fibrillation may be induced by an electric current passing through the heart during ventricular depolarization. Ventricular fibrillation is a rapid, and disorganized firing of muscle fibers within the ventricular myocardium. During ventricular fibrillation, the ventricles do not contract in an organized manner, no blood is pumped, and blood pressure falls to zero. Patient death may occur within 4 minutes from the onset of ventricular fibrillation. Other cardiac arrhythmias may occur as a result of electric current traveling through or proximate the heart during a vulnerable period. Examples of other arrhythmia's which may occur include tachycardia.

As shown in the heart equivalent circuit of FIG. 1, the heart muscle is capable of storing an electrical charge. As described previously, it is a desirable feature of the present invention that the discharge of this electrical energy is disallowed during the vulnerable periods of each heartbeat. In particular, the discharge of electrical energy stored in the heart is dissallowed in order to reduce the likelihood of unintentionally triggering ventricular fibrillation or other arrhythmia's.

Figure 3:
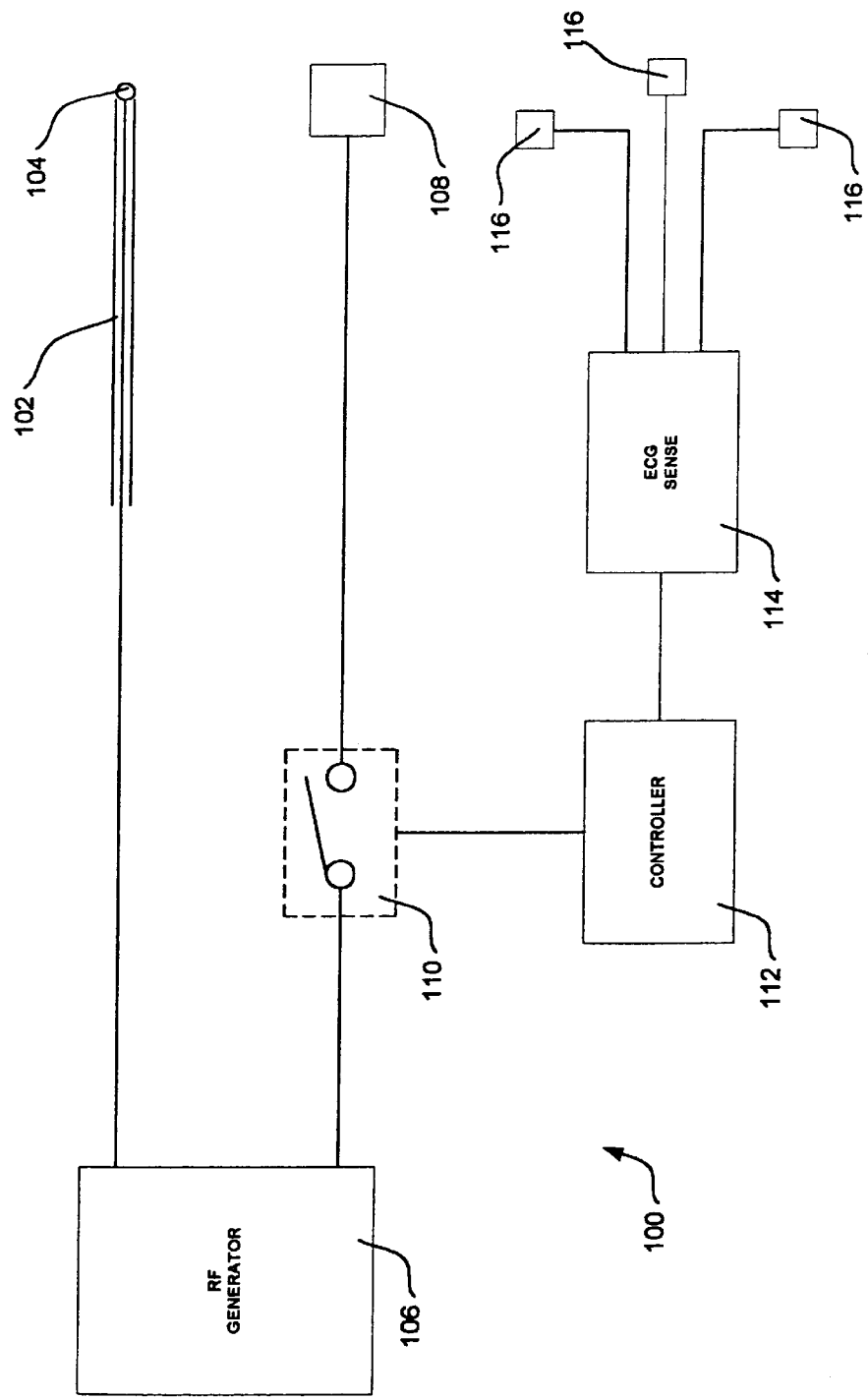
FIG. 3 is a block diagram of a PMR system in accordance with the present invention.

FIG. 3 is a block diagram of a PMR system 100 in accordance with the present invention. PMR system 100 includes a catheter 102 adapted to be received in the vasculature of a patient. An active electrode 104 is disposed on the distal end of catheter 102. Electrode 104 is coupled to a radio frequency generator 106. Generator 106 is capable of acting as a source of radio frequency energy for ablating tissue during a PMR procedure.

PMR system 100 includes a return electrode 108 which is adapted for connection to the body of a patient. Return electrode 108 in the embodiment of FIG. 3 is pictured as a flat pad. A return electrode of this type typically includes a flexible conductive pad which conforms to the contours of a patients body. Materials suitable for this conductive pad include metal foil and conductive ink disposed on a polymer substrate. Return electrodes of this type are typically adhered to the outside of a patients body with an interface material which is both conductive and sticky, such as a hydrogel adhesive. This configuration of an active electrode disposed on a cutting tool, and passive electrode pad is sometimes referred to as a monopolar configuration.

Bipolar embodiments of the present invention have also been envisioned. In a bipolar configuration, a return, or neutral electrode is disposed in close proximity to the active electrode. For example, in the embodiment of FIG. 3 a return electrode could be disposed on the outer surface of catheter 102 proximate active electrode 104. Those with skill in the art will recognize that methods and devices in accordance with the present invention may be used with bipolar or monopolar PMR techniques.

As shown in FIG. 3, a switching means 110 is coupled to both return electrode 108 and generator 106. Switching means 110 is capable of alternating between a closed circuit state and an open circuit state. When switching means 110 is in a closed circuit state it completes an electrical connection between return electrode 108 and RF generator 106. Although in the embodiment of FIG. 3, switching means 110 is coupled between generator 106 and return electrode 108, other locations for switching means 110 are possible without deviating from the spirit and scope of the present invention. For example, switching means 110 may be coupled between active electrode 104 and generator 106.

A controller 112 is coupled to switching means 110. Controller 112 is capable of changing the state of switching means 110 from an open circuit condition to a closed circuit condition or from a closed circuit condition to an open circuit condition. An electrocardiogram (ECG) signal sensing means 114 is coupled to controller 112. A plurality of ECG electrodes 116 are coupled to ECG sensing means 114. ECG electrodes 116 are adapted to make electrical contact with the body of a patient. ECG electrodes 116 may be placed on the skin, or disposed inside the body of a patient. Although three ECG electrodes 116 are illustrated in the embodiment of FIG. 3, those with skill in the art will understand that more or fewer ECG electrodes 116 may be utilized without deviating from the spirit or scope of the present invention. ECG electrodes 116 and ECG sensing means 114 are capable of collecting an ECG signal representative of a patient's cardiac rhythm.

As described above, switching means 110 is capable of creating an open circuit condition between return electrode 108 and generator 106. During a PMR procedure, switching means 110 may be utilized to reduce the likelihood of unintentionally inducing cardiac fibrillation. Switching means 110 is capable of interrupting the conduction of radio frequency energy to the patient by creating an open circuit. Switch means 110 is also capable of preventing the stored electrical charge within the patient's body from dissipating through the PMR system.

As shown in the heart equivalent circuit of FIG. 1, the heart muscle is capable of storing an electrical charge. As described previously, it is a desirable feature of the present invention that the discharge of this electrical energy is disallowed during the vulnerable periods of each heartbeat. In particular, the discharge of electrical energy stored in the heart is dissallowed in order to reduce the likelihood of unintentionally inducing ventricular fibrillation or other arrhythmia's. Creating an open circuit between the patient and the PMR system prevents electrical charge stored in the patient's body from dissipating through the PMR system.

It is an additional desirable feature of the present invention that the delivery of radio frequency to the myocardium is interrupted during vulnerable periods of the cardiac rhythm. In the embodiment of FIG. 3, switching means 110 is utilized to create an open circuit between return electrode 108 and generator 106 halting the delivery of radio frequency energy to the patient. Halting the delivery of radio frequency energy during vulnerable periods of the cardiac rhythm reduces the likelihood that ventricular fibrillation or other arrhythmia's will be induced by the PMR procedure.

As described above, ECG sensing means 114 and ECG electrodes 116 are capable of collecting an ECG signal from the patient. Controller 112 processes the ECG signal to identify vulnerable periods during which it is likely that the cardiac rhythm will be disrupted by electrical current passing through the heart or proximate the heart. In a presently preferred embodiment, controller 112 identifies the T-wave portion of the ECG signal. When controller 112 determines that the heart is in a vulnerable period, it actuates switching means 110 to an open circuit state. When the vulnerable period is over, switching means 110 may be returned to a closed state by controller 112.

A method of percutaneous myocardial revascularization in accordance with the present invention typically includes the step of introducing catheter 100 into the vasculature of the patient. Catheter 100 is preferably advanced through the vasculature of a patient until active electrode 104 is proximate the endocardium of the patient's heart. The route taken by catheter 100 will normally be by way of the femoral artery and the aorta to the left ventricle. Additional routes that may be taken include the carotid, radial and septal approach. To facilitate the advancement of catheter 100 through the vasculature of the patient, catheter 100 may include a slippery material, such as a hydrogel, disposed on its outer surfaces. Once inside the heart, active electrode 104 of catheter 100 is positioned proximate the endocardium, preferably, such that active electrode 104 is in direct contact with the endocardium. Active electrode 104 may then be energized to form a wound.

Typically, an additional step in a method in accordance with the present invention is to identify areas of tissue within the patient's heart which are candidates for PMR. To facilitate ease of discussion, areas of tissue in the heart muscle may be generally classified healthy or hibernating. Healthy tissues is tissue which is well perfused with blood, and subsequently well supplied with oxygen. Hibernating tissue is tissue which is not currently contracting to assist in the pumping of blood. However, if hibernating tissue is adequately supplied with blood, it will once again begin contracting and contributing to the pumping of blood.

A number of methods may be used to identify hibernating tissue. For example, contrast media may be injected into the coronary vessels to identify regions of the heart into which the contrast medium does not flow due to obstruction of the vessels into which the media was injected. In this case, the hibernating region will be identified by the lack of flow or abnormally low flow distally of the obstruction in the coronary vessel or vessels.

A second method which may be used to identify hibernating regions of the heart involves injecting contrast media directly into the heart chambers. Hibernating tissue may then be identified by locating areas of generally poor wall motion of the heart chambers. When this method is selected, the contrast media may be delivered to the heart chambers via catheter 100. One or more lumens may be disposed in catheter 100 to provide a suitable channel for delivering contrast media from a location outside the patient's body to the distal end of catheter 100 disposed inside the patient's body. During a PMR procedure, active electrode 104 is disposed proximate the heart tissue targeted for PMR treatment. Active electrode 104 is then energized with radio frequency energy from generator 106 and active electrode 104 proceeds to burn or ablate heart tissue. Throughout the PMR procedure, the patients ECG signal is collected by ECG sensing means 114 and monitored by controller 112. When controller 112 detects a vulnerable period of the heart's activity it sends a signal to switching means 110 causing switching means 110 to create an open circuit condition between return electrode 108 and generator 106. This open circuit condition interrupts the delivery of RF energy from active electrode 104. This open circuit condition also prevents charge stored in the heart from dissipating. Preventing electrical activity proximate the heart during vulnerable periods reduces the likelihood of unintentionally inducing ventricular fibrillation or other arrhythmias.

Figure 4:
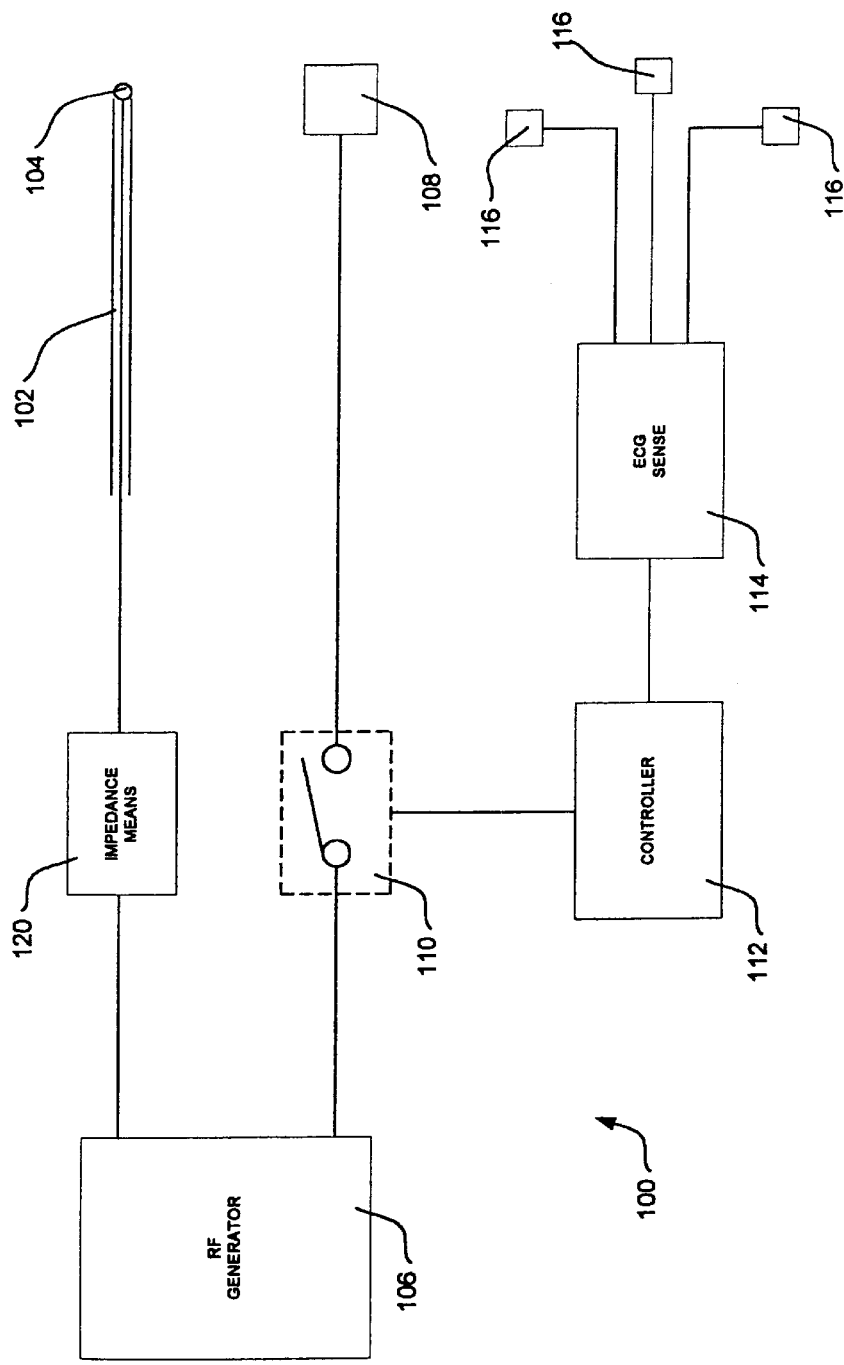
FIG. 4 is a block diagram of an alternate embodiment of a PMR system in accordance with the present invention.

FIG. 4 is a block diagram of an additional embodiment of a PMR system 100.

PMR system 100 includes a catheter 102 adapted to be received in the vasculature of a patient. An active electrode 104 is disposed on the distal end of catheter 102. Electrode 104 is coupled to an impedance means 120. Impedance means 120 is coupled to a radio frequency generator 106. As in the previous embodiment, generator 106 is capable of energizing active electrode 104 with radio frequency energy to ablate tissue during a PMR procedure.

Impedance means 120 may include active or passive components such as capacitors, inductors, resistors, transistors or the like or any combination thereof. In a presently preferred embodiment, impedance means 120 is a capacitor.

PMR system 100 includes a return electrode 108 which is adapted for connection to the body of a patient. Return electrode 108 in the embodiment of FIG. 4 is pictured as a flat pad. A return electrode of this type typically includes a flexible conductive pad which conforms to the contours of a patients body. Materials suitable for this conductive pad include metal foil and conductive ink disposed on a polymer substrate. Return electrodes of this type typically are adhered to the outside of a patients body with an interface material which is both conductive and sticky, such as a hydrogel adhesive. This configuration of active and passive electrodes is sometimes referred to as a monopolar configuration.

Bipolar embodiments of the present invention have also been envisioned. In a bipolar configuration, a return, or neutral electrode is disposed in close proximity to the active electrode. For example, in the embodiment of FIG. 4 a return electrode could be disposed on the outer surface of catheter 102 proximate active electrode 104. Those with skill in the art will recognize that methods and devices in accordance with the present invention may be used with bipolar or monopolar PMR techniques.

As shown in FIG. 4, a switching means 110 is coupled to both return electrode 108 and generator 106. Switching means 110 is capable of alternating between closed circuit and open circuit states. When switching means 110 is in a closed circuit state it completes an electrical connection between return electrode 108 and RF generator 106. Although in the embodiment of FIG. 4, switching means 110 is coupled between generator 106 and return electrode 108, other locations for switching means 110 are possible without deviating from the spirit and scope of the present invention. For example, switching means 110 may be coupled between active electrode 104 and generator 106.

A controller 112 is coupled to switching means 110. Controller 112 is capable of change the state of switching means 110 from an open circuit condition to a closed circuit condition or from a closed circuit condition to a closed circuit condition. An ECG sensing means 114 is coupled to controller 112. A plurality of ECG electrodes 116 are coupled to ECG sensing means 114. ECG electrodes 116 are adapted to make electrical contact with the body of a patient. ECG electrodes may be placed on the skin, or disposed inside the body. Although three ECG electrodes 116 are illustrated in the embodiment of FIG. 4, those with skill in the art will understand that more or fewer ECG electrodes 116 may be utilized without deviating from the spirit or scope of the present invention.

As described above, switching means 110 is capable of creating an open circuit condition between return electrode 108 and generator 106. During a PMR procedure, switching means 110 may be utilized to reduce the likelihood of unintentionally inducing cardiac fibrillation. Switching means 110 is capable of interrupting the conduction of radio frequency energy to the patient by creating an open circuit. Switch means 110 is also capable of preventing the stored electrical charge within the patient's body from dissipating through the PMR system.

The impedance value of impedance means 120 is selected so that maximum power transfer will occur when active electrode 104 is in contact with the myocardial or endocardial tissue of the patient's heart. To accomplish this, the impedance value of impedance means 104 is selected so that impedance of the PMR system is substantially equal to the load impedance which will be encountered when the active electrode contacts the myocardial or endocardial tissue of the patient's heart.

As described above, maximum power transfer occurs when the impedance of the PMR system is equal to the load impedance. This relationship may be demonstrated mathematically beginning with an equation describing the average power delivered to the load (i.e. the patient).

$$P = |I|^2 R_L \qquad \text{Equation 1}$$

Where I is the load current and $R_L$ is the resistance of the load. Load current may be calculated as follows:

$$I = \frac{V_{Th}}{(R_{Th} + R_L) + j(X_{Th} + X_L)} \qquad \text{Equation 2}$$

Where $R_{Th}$ is the Thevenin equivalent impedance of the PMR system and $V_{Th}$ is the Thevenin equivalent voltage delivered by the PMR system.

Substituting equation 2 into equation 1 yields:

$$P = \frac{|V_{Th}|^2 R_L}{(R_{Th} + R_L)^2 + (X_{Th} + X_L)^2} \qquad \text{Equation 3}$$

P will be maximized when $dP/dR_L$ and $dP/dX_L$ are both zero.

$$\frac{\partial P}{\partial X_L} = \frac{-|V_{Th}|^2 2 R_L (X_L + X_{Th})}{[(R_L + R_{Th})^2 + (X_L + X_{Th})^2]^2} \qquad \text{Equation 4}$$

$$\frac{\partial P}{\partial R_L} = \frac{|V_{Th}|^2 [(R_L + R_{Th})^2 + (X_L + X_{Th})^2 - 2R_L(R_L + R_{Th})]}{[(R_L + R_{Th})^2 + (X_L + X_{Th})^2]^2} \qquad \text{Equation 5}$$

An evaluation equation 5 reveals that $dP/dX_L$ will be zero when:

$$X_L = X_{Th} \qquad \text{Equation 6}$$

An evaluation of equation 6 reveals that $dP/dR_L$ will be zero when:

$$R_L = \sqrt{R^2_{Th} + (X_L + X_{Th})^2} \qquad \text{Equation 7}$$

An examination of equations 7 and 8 reveals that both derivatives will be zero when:

$$Z_L = Z^*_{Th}$$ Equation 8

The maximum average power is delivered to the load when $Z_L$ is equal to the conjugate of $Z_{Th}$. In one embodiment of the present invention, the load impedance when the active electrode contacts myocardial tissue is equal to the conjugate of the impedance of the PMR system. It should be understood that other embodiments of the present invention are possible. For example the impedance of the PMR system may be a value which is not an exact conjugate match to the impedance of the patient without deviating from the spirit and scope of the present invention. For example, in some applications it may be adequate for the impedance of the PMR system to be substantially equal to the load impedance when the active electrode contacts the myocardial tissue.

If active electrode 104 loses contact with the myocardial tissue of the patient's heart during a PMR procedure, the load impedance value will change to a value which is not equal to the impedance of the PMR system. When the load impedance is no longer matched to the impedance of the PMR system, the level of power transfer will be reduced. As described previously it is a desirable feature of the present invention to reduce the power level used during a PMR procedure when the active electrode is not properly positioned.

The resulting impedance mismatch causes a reduction in the power transferred by the PMR system. It is a desirable feature of this embodiment of a PMR system that the power transferred to the patient is reduced at times when the active electrode is not in contact with myocardial tissue. In clinical use, this situation may occur when the motion of the heart walls due to the blood pumping action of the heart causes the active electrode to lose contact with the myocardial tissue for a period of time during a PMR procedure. Contact between the active electrode and the myocardial tissue may also be lost due to the difficulties inherent in the use of minimally invasive surgical techniques.

A method of percutaneous myocardial revascularization in accordance with the embodiment of FIG. 4 typically includes the step of introducing catheter 100 into the vasculature of the patient. Catheter 100 is preferably advanced through the vasculature of a patient until active electrode 104 is proximate the endocardium of a patient's heart. The route taken by catheter 100 will normally be by way of the femoral artery and the aorta to the left ventricle. Additional routes which may be taken include carotid, radial and septal approaches. To facilitate the advancement of catheter 100 through the vasculature of the patient, catheter 100 may include a slippery material, such as a hydrogel disposed on its outer surfaces.

Once inside the heart, active electrode 104 of catheter 100 is positioned proximate the heart tissue targeted for PMR therapy. It is preferred that active electrode 104 be in direct contact with the myocardium or the endocardium. Active electrode 104 is then energized with radio frequency energy from generator 106. If active electrode 104 is in contact with the myocardium/endocardium when active electrode 104 is energized, the transfer of energy from the PMR system to the patient will be maximized from the outset. If active electrode 104 is not in contact with the myocardium/endocardium when active electrode 104 is energized, energy will be transferred to the patient at a lower level.

If active electrode 104 loses contact with the myocardial tissue of the patent's heart, the load impedance value will change to a value which is not equal to the impedance of the PMR system. When the load impedance is no longer matched to the impedance of the PMR system, the level of power transfer will be reduced. As described previously it is a desirable feature of the present invention that the power is reduced when the active electrode is not properly positioned.

In a clinical environment, active electrode 104 may lose contact with the heart tissue due to the blood pumping action of the heart. Contact between the active electrode and the myocardial tissue may also be lost due to the difficulties inherent in the use of minimally invasive surgical techniques. When these events occur, the resulting impedance mismatch causes a reduction in the power transferred by the PMR system. It is a desirable feature of this embodiment of a PMR system that the power transferred to the patient is reduced at times when the active electrode is not in contact with myocardial tissue.

Figure 5:
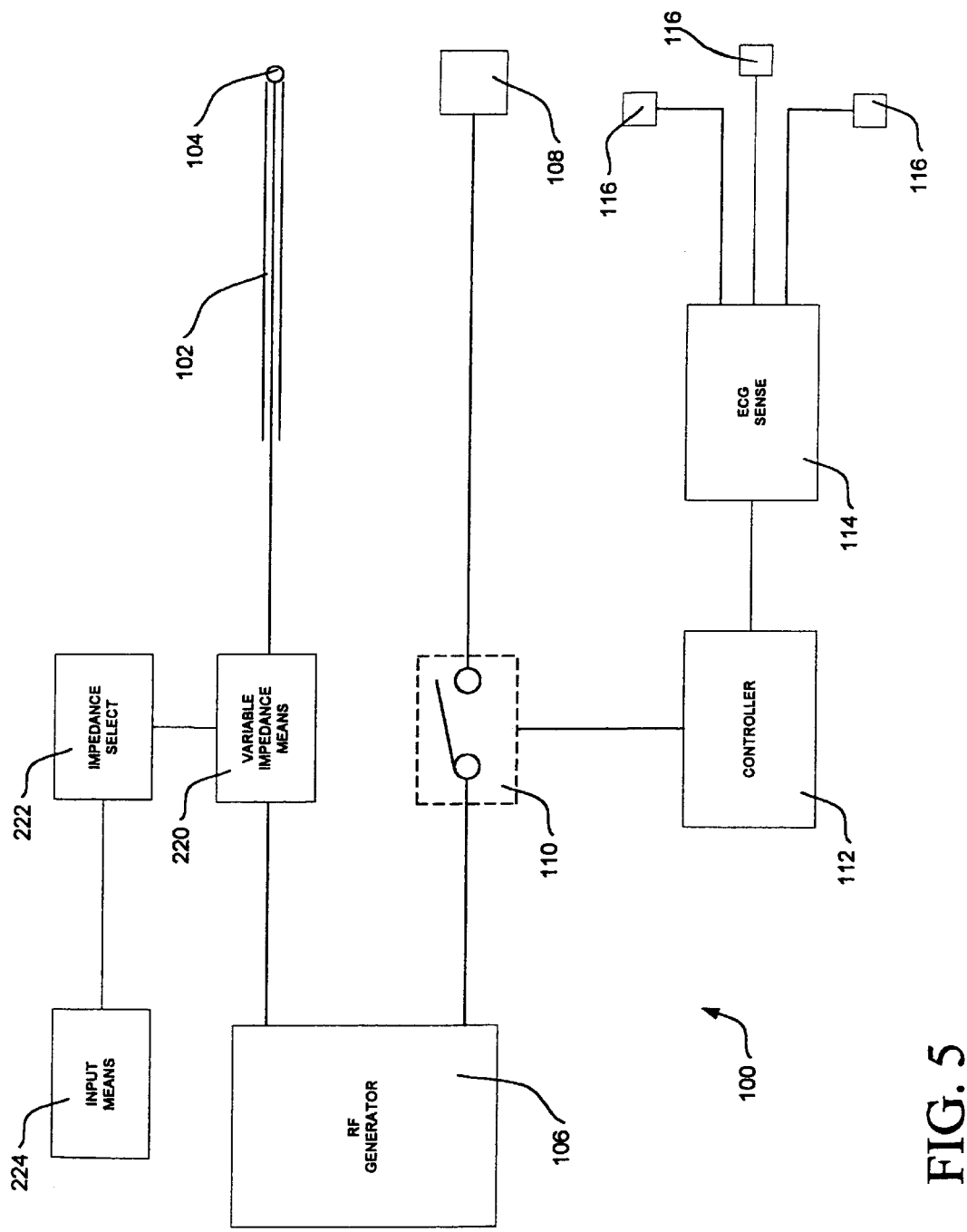
FIG. 5 is a block diagram of an additional embodiment of a PMR system in accordance with the present invention.

FIG. 5 is a block diagram of an additional embodiment of a PMR system 100. PMR system 100 includes a catheter 102 adapted to be received in the vasculature of a patient. An active electrode 104 is disposed on the distal end of catheter 102. Electrode 104 is coupled to an variable impedance means 220. Variable impedance means 220 is coupled to a radio frequency generator 106. As in the previous embodiments, generator 106 is capable of energizing active electrode 104 with radio frequency energy to ablate tissue during a PMR procedure.

As described above, the embodiment of PMR system 100 illustrated in FIG. 5 includes a variable impedance means 220. Variable impedance means 220 is coupled to an impedance selection means 222. Impedance selection means 222 is coupled to an input means 224. Input means 224 provides a physician or other user of PMR system 100 to enter information pertaining to the PMR procedure presently being preformed. This information may include the model number of catheter 102, the surface area of active electrode 104, the weight of the patient, the desired voltage, etc.

Variable impedance means 220 may include active or passive components such as capacitors, inductors, resistors, transistors or the like, or any combination thereof. In a presently preferred embodiment, variable impedance means 220 is a network of capacitors and solid state switching devices. In this presently preferred embodiment, the impedance of variable impedance means may be varied by switching capacitors in or out of the network. The impedance value of variable impedance means 220 is selected by impedance selection means 222. In the preferred embodiment described above, impedance selection means 222 controls the state of the solid state switches in variable impedance means 220.

Information entered into PMR system 100 via input means 224 is utilized to select an appropriate value for variable impedance means 220. In a presently preferred embodiment, the impedance value selected by impedance selection means 222 is based on the geometry of active electrode 104 included in a particular catheter 100. Also in a presently preferred embodiment, impedance selection means 222 includes stored information useful for selecting an appropriate impedance value. This information may include impedance values appropriate for each model of catheter and each voltage level. Other factors may be used in determining appropriate impedance values without deviating from the spirit or scope of the present invention. In any case, the impedance value of variable impedance means 220 is selected so that maximum power transfer occurs when active electrode 104 is in contact with myocardial/endocardial tissue.

A method of percutaneous myocardial revascularization in accordance with the embodiment of FIG. 5 typically begins with the step of entering information pertaining to the PMR procedure presently being performed. A physician or other user of PMR system 100 may enter this information via input means 224. Impedance selection means 222 uses the information entered via input means 224 along with information stored in memory to select an appropriate impedance value for the present PMR procedure.

A method of percutaneous myocardial revascularization in accordance with the embodiment of FIG. 5 also typically includes the step of introducing catheter 100 into the vasculature of the patient. Catheter 100 is preferably advanced through the vasculature of a patient until active electrode 104 is proximate the endocardium of a patient's heart. The route taken by catheter 100 will normally be by way of the femoral artery and the aorta to the left ventricle. Additional routes which may be taken include carotid, radial and septal approaches. To facilitate the advancement of catheter 100 through the vasculature of the patient, catheter 100 may include a slippery material, such as a hydrogel disposed on its outer surfaces.

Once inside the heart, active electrode 104 of catheter 100 is positioned proximate the heart tissue targeted for PMR therapy. It is preferred that active electrode 104 be in direct contact with the myocardium or the endocardium. Active electrode 104 is then energized with radio frequency energy from generator 106. If active electrode 104 is in contact with the myocardium/endocardium when active electrode 104 is energized, the transfer of energy from the PMR system to the patient will be maximized from the outset. If active electrode 104 is not in contact with the myocardium/endocardium when active electrode 104 is energized, energy will be transferred to the patient at a lower level.

If active electrode 104 loses contact with the myocardial tissue of the patent's heart, the load impedance value will change to a value which is not equal to the impedance of the PMR system. When the load impedance is no longer matched to the impedance of the PMR system, the level of power transfer will be reduced. As described previously it is a desirable feature of the present invention that the power is reduced when the active electrode is not properly positioned.

In a clinical environment, active electrode 104 may lose contact with the heart tissue due to the blood pumping action of the heart. Contact between the active electrode and the myocardial tissue may also be lost due to the difficulties inherent in the use of minimally invasive surgical techniques. When these events occur, the resulting impedance mismatch causes a reduction in the power transferred by the PMR system. It is a desirable feature of this embodiment of a PMR system that the power transferred to the patient is reduced at times when the active electrode is not in contact with myocardial tissue.

Figure 6:
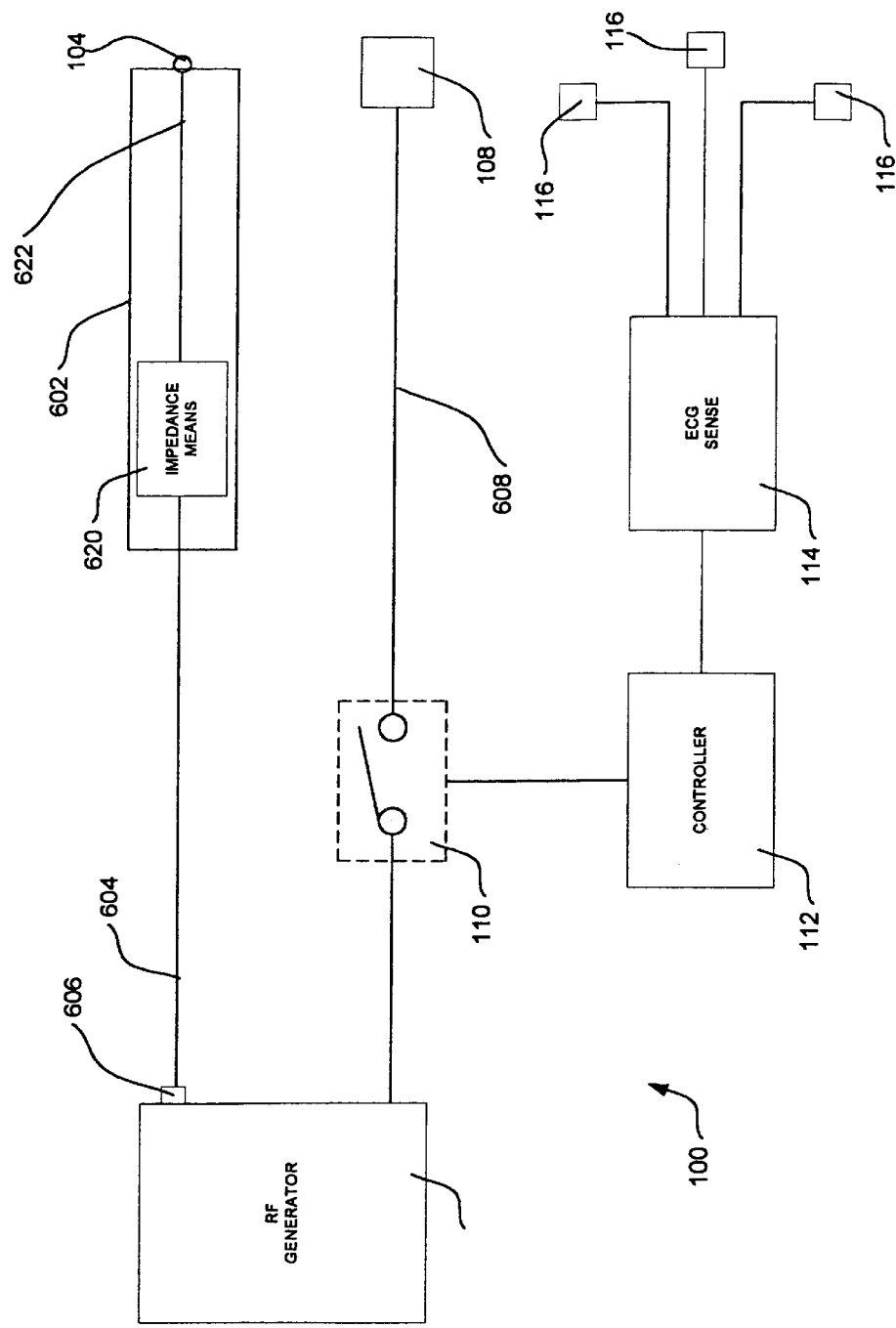
FIG. 6 is a block diagram of an additional embodiment of a PMR system in accordance with the present invention.

FIG. 6 is a block diagram of an additional embodiment of a PMR system 100. PMR system 100 includes a tuned catheter 602 adapted to be received in the vasculature of a patient. Tuned catheter 602 includes a lead wire 604. Lead wire 604 is adapted to make a connection to a radio frequency generator 106 via a connection means 606. Tuned catheter 602 may be comprised of an elongate shaft having a distal end and a proximal end. Tuned catheter may also include a lumen extending from the distal end to the proximal end.

An impedance means 620 and a conductor 622 are disposed within tuned catheter 602. An active electrode 104 is disposed on the distal end of catheter 602. Active electrode 104 is electrically connected to generator 106 via conductor 622, impedance means 620 and lead wire 604. Generator 106 is capable of energizing active electrode 104 with radio frequency energy to ablate tissue during a PMR procedure. PMR system 100 includes a return electrode 108 which is adapted for connection to the body of a patient. Return electrode 108 is coupled to generator 106 via a return lead wire 608 and a switching means 110.

Impedance means 620 may include active or passive components such as capacitors, inductors, resistors, and transistors, or the like or any combination thereof. In a presently preferred embodiment, impedance means 620 is a capacitor. The impedance value of impedance means 620 is selected so that maximum power transfer will occur when active electrode 104 is in contact with the myocardial tissue of the patient's heart. To accomplish this, the impedance value of impedance means 620 is selected so that impedance of the PMR system is substantially equal to the load impedance which will be encountered when the active electrode contacts the myocardial tissue of the patients heart during a PMR procedure.

If active electrode 104 loses contact with the myocardial tissue of the patent's heart, the load impedance value will change to a value which is not equal to the impedance of the PMR system. When the load impedance is no longer matched to the impedance of the PMR system, the level of power transfer will be reduced. As described previously it is a desirable feature of the present invention to reduce the power level used during a PMR procedure when the active electrode is not properly positioned.

The resulting impedance mismatch causes a reduction in the power transferred by the PMR system. It is a desirable feature of this embodiment of a PMR system that the power transferred to the patient is reduced at times when the active electrode is not in contact with myocardial tissue. In clinical use, the situation may occur when the motion of the heart walls due to the blood pumping action of the heart cause the active electrode to lose contact with the myocardial tissue for a period of time during a PMR procedure. Contact between the active electrode and the myocardial tissue may also be lost due to the difficulties inherent in the use of minimally invasive surgical techniques.

A method of percutaneous myocardial revascularization in accordance with the embodiment of FIG. 6 typically begins with the step of selecting a catheter for the present procedure. A physician may select a catheter based on personal preference, patient dependent parameters, or other factors. A catheter in accordance with the embodiment of FIG. 6 is tuned so that maximum power transfer will occur when active electrode 104 is in contact with myocardial/endocardial tissue.

A method of percutaneous myocardial revascularization in accordance with the embodiment of FIG. 6 also typically includes the step of introducing the selected catheter into the vasculature of the patient. Catheter 100 is preferably advanced through the vasculature of a patient until active electrode 104 is proximate the endocardium of a patient's heart. The route taken by catheter 100 will normally be by way of the femoral artery and the aorta to the left ventricle. Additional routes which may be taken include carotid, radial and septal approaches. To facilitate the advancement of catheter 100 through the vasculature of the patient, catheter 100 may include a slippery material, such as a hydrogel disposed on its outer surfaces.

Once inside the heart, active electrode 104 of catheter 100 is positioned proximate the heart tissue targeted for PMR therapy. It is preferred that active electrode 104 be in direct contact with the myocardium or the endocardium. Active electrode 104 is then energized with radio frequency energy from generator 106. If active electrode 104 is in contact with the myocardium/endocardium when active electrode 104 is energized, the transfer of energy from the PMR system to the patient will be maximized from the outset. If active electrode 104 is not in contact with the myocardium/endocardium when active electrode 104 is energized, energy will be transferred to the patient at a lower level.

If active electrode 104 loses contact with the myocardial tissue of the patent's heart, the load impedance value will change to a value which is not equal to the impedance of the PMR system. When the load impedance is no longer matched to he impedance of the PMR system, the level of power transfer will be reduced. As described previously it is a desirable feature of the present invention that the power is reduced when the active electrode is not properly positioned.

In a clinical environment, active electrode 104 may lose contact with the heart tissue due to the blood pumping action of the heart. Contact between the active electrode and the myocardial tissue may also be lost due to the difficulties inherent in the use of minimally invasive surgical techniques. When these events occur, the resulting impedance mismatch causes a reduction in the power transferred by the PMR system. It is a desirable feature of this embodiment of a PMR system that the power transferred to the patient is reduced at times when the active electrode is not in contact with myocardial tissue.

Figure 7:
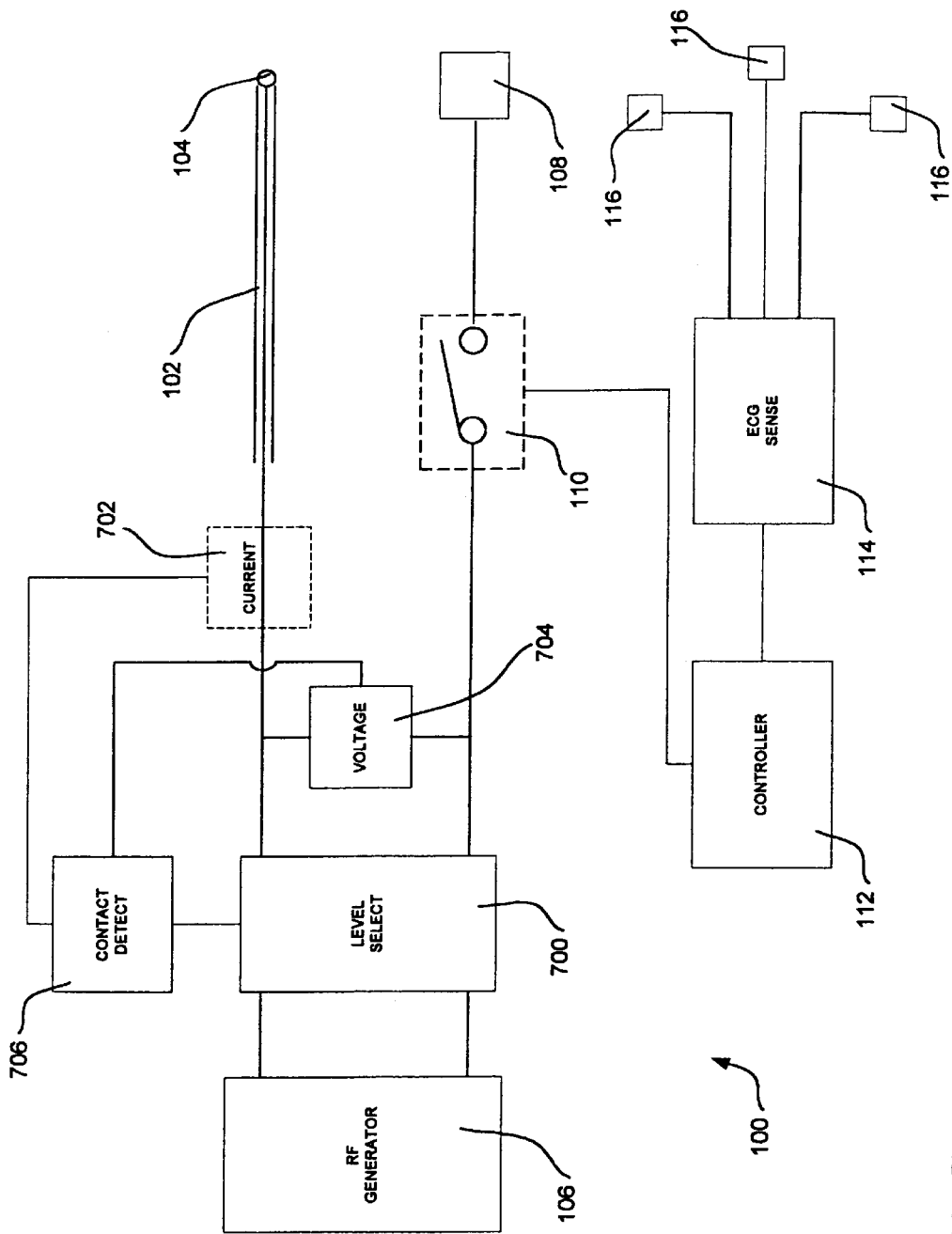
FIG. 7 is a block diagram of an additional embodiment of a PMR system in accordance with the present invention.

FIG. 7 is a block diagram of an additional embodiment of a PMR system 100 in accordance with the present invention. The embodiment illustrated in FIG. 7, is a PMR system 100 for use with a method of PMR which detects contact between active electrode 104 and myocardial tissue. Detection of myocardial tissue occurs with a relatively low level of power being delivered to active electrode 104. PMR system 100 of FIG. 7 is capable of selectively applying a higher level of radio frequency energy when contact between active electrode 104 and the myocardial tissue has been detected.

PMR system 100 includes a catheter 102 adapted to be received in the vasculature of a patient. An active electrode 104 is disposed on the distal end of catheter 102. A level selection means 700 is coupled to active electrode 104 and a radio frequency generator. As in the previous embodiments, generator 106 is capable of energizing active electrode 104 with radio frequency energy. Level selector 700 and generator 106 are adapted to selectively apply two levels of power to active electrode 104. A relatively low level of power is used to detect contact between active electrode 104 and myocardial tissue. Once contact between active electrode 104 and myocardial tissue has been detected, a higher level of radio frequency energy may be applied to active electrode 104 to ablate or bum tissue.

PMR system 100 of FIG. 7 also includes a current sensing means 702 which is capable of measuring the level of current delivered to active electrode 104 by generator 106 and level selector 700. Current transducers suitable for use in current sensing means 702 are commercially available. For example, a current sensor suitable for some applications is commercially available from LEM USA, Inc. of Milwaukee Wis.

Additionally, PMR system 100 of FIG. 7 includes a voltage sensing means 704 which is capable of measuring the level of voltage delivered to active electrode 104 by generator 106 and level selector 700. Voltage transducers suitable for use in voltage sensing means 704 are commercially available. For example, a voltage sensor suitable for some applications is commercially available from LEM USA, Inc. of Milwaukee Wis.

A means of detecting contact 706 is coupled to current sensing means 702 and voltage sensing means 706. Contact detecting means 706 is capable of detecting contact between active electrode 104 and myocardial tissue. Contact detecting means 706 is capable of monitoring, storing, and processing voltage and current waveforms from voltage sensing means 704 and current sensing means 702. Contact detecting means 706 is also coupled to level selector 700. In a presently preferred embodiment, contact detecting means 706 creates a signal which enables level selector 700 to selectively apply a higher level of radio frequency energy to active electrode 104.

Figure 8:
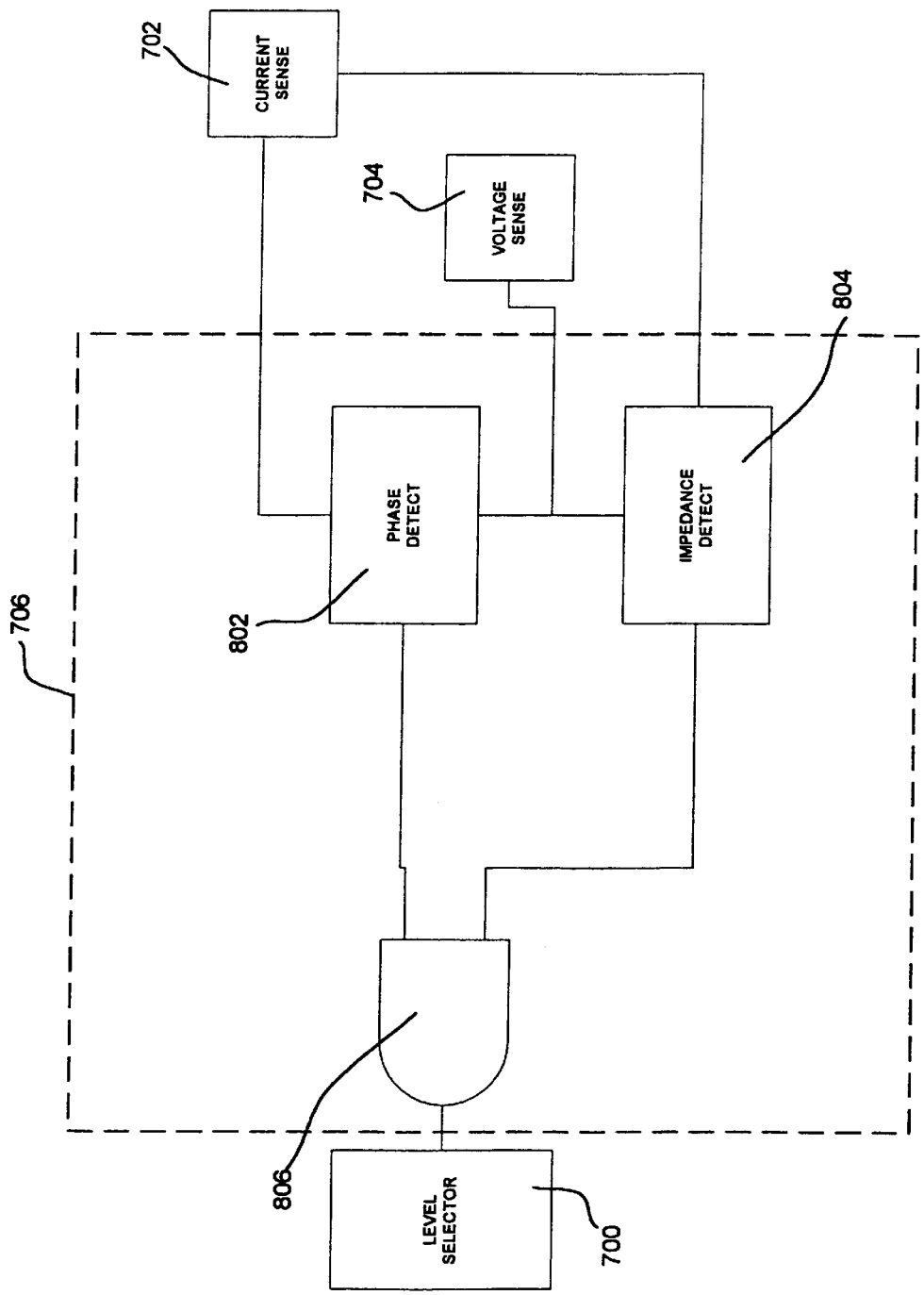
FIG. 8 is a block diagram illustrating one embodiment of a contact detecting means in accordance with the present invention.

FIG. 8 is a block diagram illustrating one embodiment of contact detecting means 706. In the embodiment of FIG. 8, contact detecting means 706 includes a phase detecting means 802 which is coupled to voltage sensing means 704, current sensing means 702 and a logic operator 806. Phase detect means 802 is capable of measuring the phase angle between the current waveform and the voltage waveform. In a presently preferred embodiment, phase detect means 802 outputs a logic high signal to logic operator 806 when the phase angle between the current waveform and the voltage waveform is greater than 40 degrees.

Contact detecting means 706 of FIG. 8 also includes an impedance detecting means 804 coupled to current sensing means 702, voltage sensing means 704, and logic operator 806. Impedance detecting means 804 is capable calculating the impedance between active electrode 104 and return electrode 108. In a presently preferred embodiment, impedance detecting means 804 outputs a logic high signal to logic operator 806 when the measured impedance is greater than 300 ohms.

As shown in FIG. 8, logic operator 806 performs an AND function on the signals received from phase detecting means 802 and impedance detecting means 804. Logic operator 806 is coupled to level selector 700. In a presently preferred embodiment, a high level enable signal is sent to level selector 700 by logic operator 806 when the load impedance is greater than 300 ohms, and the phase angle between the current waveform and the voltage waveform is greater than 40 degrees.

It should be understood that other embodiments of contact detecting means 706 are possible without deviating from the spirit and scope of the present invention. For example, contact may be detected based solely on the measured impedance. Alternately, contact may be detected based solely on the measured phase angle. It should also be understood that the values given above for phase angle and impedance are examples and other values may be utilized without deviating from the spirit or scope of the invention.

The embodiment illustrated in FIG. 7, is a PMR system 100 for use with a method of PMR during which a high level of radio frequency energy is not applied to active electrode 104 until contact between active electrode 104 and myocardial tissue has been detected. As described above, level selector 700 is capable of selectively applying two levels of radio frequency energy to active electrode 104. A relatively low level of radio frequency energy is utilized to detect contact between active electrode 104 and myocardial tissue. A higher level of radio frequency energy is selectively applied to active electrode 104 after contact has been verified, to begin ablating or burning tissue.

A method of percutaneous myocardial revascularization in accordance with the embodiment of FIG. 7 typically includes the step of introducing catheter 100 into the vasculature of the patient. Catheter 100 is preferably advanced through the vasculature of a patient until active electrode 104 is proximate the endocardium of a patient's heart. The route taken by catheter 100 will normally be by way of the femoral artery and the aorta to the left ventricle. Additional routes which may be taken include carotid, radial and septal approaches. To facilitate the advancement of catheter 100 through the vasculature of the patient, catheter 100 may include a slippery material, such as a hydrogel disposed on its outer surfaces.

Once inside the heart, active electrode 104 of catheter 100 is positioned proximate the heart tissue targeted for PMR therapy. Active electrode 104 is then energized with a low level of radio frequency energy. Measurements are then made to determine if active electrode 104 is in contact with endocardial or myocardial tissue. In a presently preferred embodiment, the phase angle between the current waveform and the voltage wave form is measured. Also in a presently preferred embodiment, the impedance of the patient is measured. If the measured values are within an acceptable range of values, a higher level of radio frequency energy is applied to active electrode 104 to form a wound.

A PMR method in accordance with the present invention, may include the step of delivering a fluid to the wound site via catheter 102. Contact detecting means 706 may be used to verify that distal end 18 is proximate myocardial tissue before delivering the fluid. This fluid may include saline, radiopaque contrast media, a therapeutic agent, a caustic agent, or any combination of these. Injecting a fluid including a radiopaque contrast media into the wound serves to create a radiopaque marker of a treatment site. Injecting a fluid, including a therapeutic agent, serves to promote angiogenisis. The formation of the wound may also be enhanced by collateral damage to the myocardium induced by directing pressurized fluid into the wound site. The impact of the pressurized fluid causes vessels, capillaries, and sinuses to rupture.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A system for performing percutaneous myocardial revascularization on a portion of a human heart, comprising:
    an active electrode disposed at the end of a catheter;
    a radio frequency generator coupled to the active electrode for delivering radio frequency energy thereto;
    a return electrode adapted for connection to the body of a patient;
    a means for switching coupled to the return electrode and the radio frequency generator;
    the switching means having a closed circuit state and an open circuit state;
    wherein the switching means is configured such that an electrical charge stored in the human heart is prevented from dissipating through the system when the switching means assumes the closed circuit state;
    a means for patient monitoring capable of detecting electrical activity in the heart of a patient; and
    a controller coupled to the means for patient monitoring and the means for switching,
    the controller being capable of detecting a vulnerable period in the activity of the heart and responding by directing the means for switching to create an open circuit.

2. A system for performing percutaneous myocardial revascularization on a portion of a human heart, comprising:
    an active electrode disposed proximate a distal end of a catheter;
    a radio frequency generator having an output terminal coupled to the active electrode;
    a return electrode adapted for connection to the body of a patient;
    a means for switching coupled between the return electrode and a ground terminal of the radio frequency generator;
    the means for switching having an closed circuit state in which current may pass between the return electrode and the ground terminal of the radio frequency generator, and a open circuit state in which current is prevented from passing between the return electrode and the ground terminal of the radio frequency generator; and
    wherein the switching means is configured such that an electrical charge stored in the human heart is prevented from dissipating through the system when the switching means assumes the open circuit state.

3. The system of claim 2, further including a controller coupled to the means for switching for providing an enable signal to the means for switching, the enable signal controlling whether the means for switching is in the closed circuit state or the open circuit state.

4. The system of claim 3, further including a means for patient monitoring coupled to the controller.

5. The system of claim 4, wherein the means for patient monitoring is adapted to sense a physiological signal indicative of the cardiac rhythm of the patient.

6. The system of claim 5, wherein the means for switching and the means for patient monitoring are configured such that the means for switching is placed in the open circuit state during a vulnerable portion of the cardiac rhythm.

7. The system of claim 5, wherein the means for switching and the means for patient monitoring are configured such that the means for switching is placed in the open circuit state during a repolarization portion of the cardiac rhythm.

8. The system of claim 5, wherein the means for switching and the means for patient monitoring are configured such that the means for switching is placed in the open circuit state during a T-wave portion of the cardiac rhythm.

* * * * *